United States Patent [19]

Cudmore

[11] Patent Number: 4,578,502

[45] Date of Patent: Mar. 25, 1986

[54] POLYETHYLENE TEREPHTHALATE SAPONIFICATION PROCESS

[76] Inventor: Warner J. G. Cudmore, 25847 Ashwood Dr., Sun Lakes, Ariz. 85224

[21] Appl. No.: 693,248

[22] Filed: Jan. 22, 1985

[51] Int. Cl.$^4$ ............... C07C 67/60; C07C 51/487
[52] U.S. Cl. ............... 560/79; 528/308.1; 528/308.3; 528/308.4; 528/308.8; 562/483; 562/485; 562/486; 562/487; 568/858
[58] Field of Search ............... 562/483, 485, 486, 487; 568/858; 528/308.1, 308.3, 308.4, 308.8; 560/79

[56] References Cited

U.S. PATENT DOCUMENTS 3,223,731 12/1965 Craig ............... 562/483

Primary Examiner—Natalie Trousof
Assistant Examiner—Vera C. Clarke
Attorney, Agent, or Firm—Trask & Britt

[57] ABSTRACT

Solid scrap polyethylene terephthalate (PET) resin may be reprocessed by depolymerizing said scrap in the presence of water or methanol, recovering the monomers resulting from the depolymerization reaction and repolymerizing the monomers to form polymeric polyethylene phthalate.

22 Claims, 1 Drawing Figure

POLYETHYLENE TEREPHTHALATE SAPONIFICATION PROCESS

BACKGROUND OF THE INVENTION

1. Field:

This invention relates to the recovery of monomeric components from condensation-type linear polyester resins such as high molecular weight polyethylene terephthalate (PET), and the repolymerization of such monomers.

2. State of the Art:

Prior efforts regarding reuse of high molecular weight polymer PET have been directed to reuse either in the existing polymerized form, e.g. by grinding and using as filler material, etc. or by partially depolymerizing in the presence of a monomer to a limited extent to produce a low molecular weight polymer, e.g. as disclosed in U.S. Pat. No. 3,703,488 of Morton.

Morton suggests that complete depolymerization to a terephthalic acid or dimethyl terephthalate has been proposed but has not been satisfactory. Morton refers to British Pat. No. 610,136 as disclosing a depolymerization process using large excesses of glycol. The process of Morton, however, depolymerizes scrap PET merely to a lower molecular weight PET resin by high temperature extrusion of the solid, scrap PET resin with significant addition of glycol. Such extruded low molecular weight PET resin is included in amounts up to about 20% by weight with fresh glycol esters or fresh prepolymers so that objectionable color in the final product can be avoided.

Depolymerization of PET is suggested in MacDowell, U.S. Pat. No. 3,222,299. MacDowell describes a process for heating scrap PET in the presence of glycol to form a diglycol terephthalate, which can be used in minor amounts in a polyesterification process for forming PET from freshly prepared diglycol ester of terephthalic acid in the presence of an aromatic sulfonate compound containing an alkali or alkaline earth metal.

In MacDowell's process, all the catalysts, dyes, pigments, stabilizers, etc. present in the fibrous waste polyester are fed into the prepolymerizer and into the final polymerizer. Furthermore, the diglycol therephthalate ester prepared in the reactor of MacDowell requires quantities of fresh dimethyl terephthalate to be introduced into the ester exchange column. Also significant quantities of fresh glycol, actually equimolar amounts with respect to the fresh dimethyl terephthalate, must be introduced into the reactor in order to form diglycol terephthalate. Therefore, the catalysts, dyes, pigments, stabilizers, etc. present in the original solid scrap PET are present in the final polymer except their concentrations in the final polymer are only one-half their concentration in the original scrap PET.

MacDowell further discloses that polyesterification of the diglycol terephthalate does not occur unless sodium 3,5-dicarboxybenzenesulfonate is present.

U.S. Pat. No. 3,988,406 of Nakamura, et al. also utilizes a process somewhat similar to MacDowell for causing some depolymerization of scrap PET in the presence of substantial quantities of ethylene glycol after the scrap PET fibers have been formed into a fibrous rod about six millimeters in diameter and about 30 millimeters in length.

Numerous patents disclose various treatments of PET scrap to utilize such scrap in an economic manner. Patents disclosing such techniques are as follows: U.S. Pat. No. 4,193,896 of Cook; U.S. Pat. No. 4,368,274 of Scott; and U.S. Pat. Nos. 4,003,880; 4,003,881; and 4,118,187 of Sidebotham, et al.

DESCRIPTION OF THE INVENTION

Figure 1:
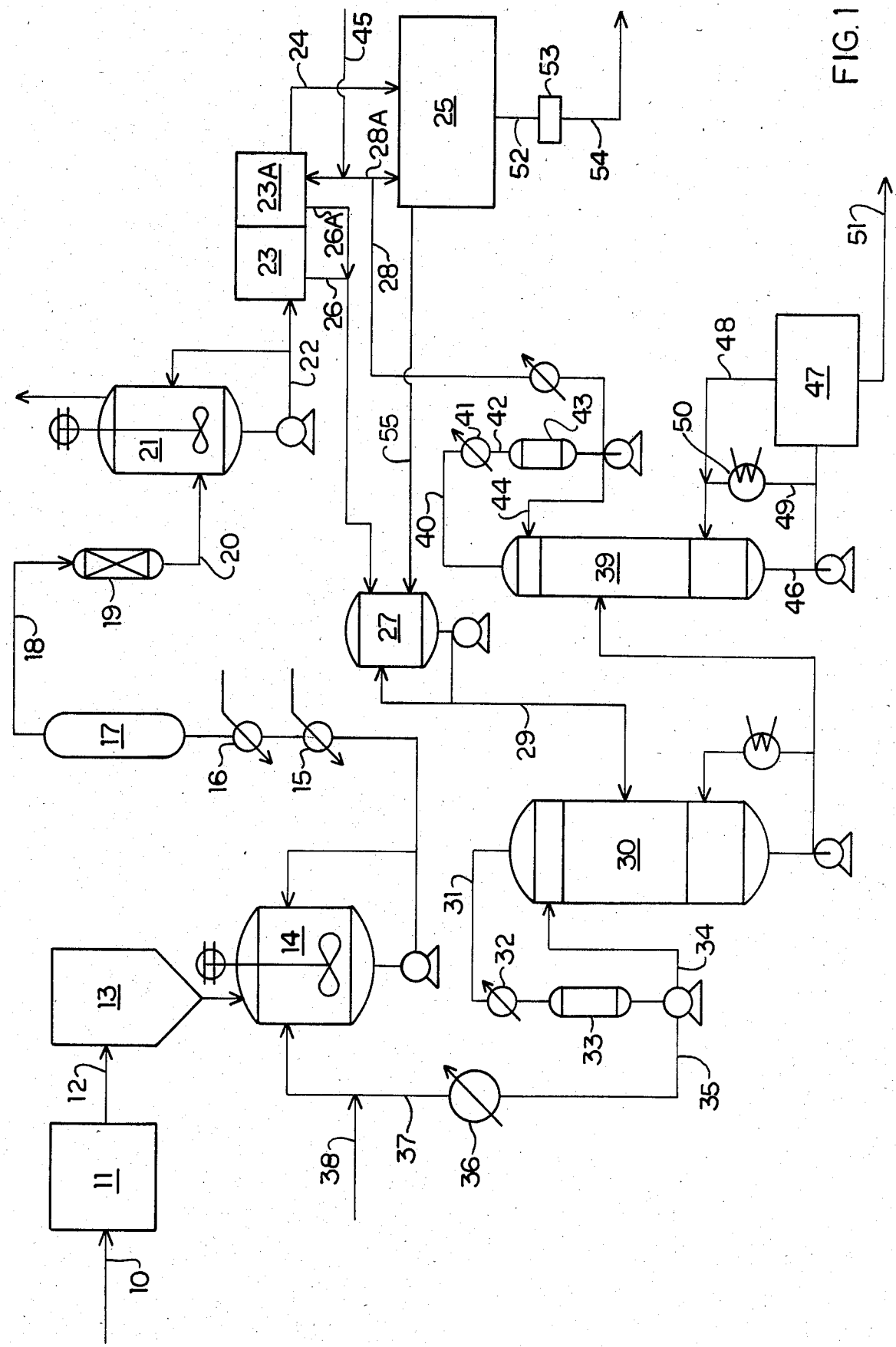
FIG. 1 is a schematic flow diagram of the scrap polyethylene terephthalate (PET) depolymerization monomer recovery and repolymerization process of the instant invention.

A process has been invented for the efficient, energy conservative, substantially complete depolymerization of condensation-type linear polyester resins to monomers such as terephthalic acid, dimethyl terephthalate, ethylene glycol and the like. The process has particular application to PET which may be depolymerized to its monomers, terephthalic acid and ethylene glycol, in ratios appropriate for the repolymerization of said monomers to PET with only slight make-up of ethylene glycol.

Scrap PET represents a large disposal problem and expense to manufacturers and users of PET. Existing techniques for recovery and utilization of scrap PET have not been particularly satisfactory technically or economically. Many of such existing processes are directed to utilization of scrap PET in more or less its original form as filler additions to virgin PET materials.

Scrap PET typically contains catalysts, dyes, pigments, stabilizers, ultraviolet light radiation protectors, etc. The type of dye, pigment, stabilizer, etc. used in PET for one end product may differ significantly from those used in another end product. Thus, scrap from one product line may not be readily utilizable as filler in another product line. Also, even in production of an identical product, the amount of PET used as "filler" may be very limited. (Filler is mechanically contained in an end product; it is not chemically interlinked with other PET in the product.) Significant amounts of a filler, even scrap PET, in a PET product may have a detrimental effect upon the properties of a PET product in comparison with an "unfilled" PET product of a similar molecular weight and with similar other modifiers.

The reconversion of PET to monomer form requires a process, such as that disclosed herein, which is energy and materials efficient and which produces monomers essentially uncontaminated by catalysts, dyes, pigments, stabilizers, etc. present in the original scrap PET material.

The instant invention comprises a process for recovering monomeric polycarboxylic acids an polyols from solid scrap, high molecular weight, condensation-type, polyalkylene phthalate polyester resins, particularly polyethylene phthalate resins, comprising the following steps:

1. Granulating said scrap resin into resin particles sufficiently minute to be readily slurried.

2. Slurrying said resin particles with sufficient solvent such as water or methanol to prepare a readly pumpable slurry.

3. Depolymerizing said slurried resin by application of heat and pressure for a time sufficient to convert substantially all of said resin into its monmeric components in liquid form as a mixture of a monomeric polycarboxylic acid or a dimethyl ester thereof, and a polyol, typically a lower alkylene diol such as ethylene glycol, dissolved in said solvent. Such a depolymerization reaction is occasionally referred to as hydrolysis whenever water is the solvent. It may also be referred to as methanolysis whenever methanol is the solvent.

4. Crystallizing substantially all of the monomeric polycarboxylic acid present in said mixture by flash crystallizing said mixture.

5. Recovering said crystallized monomeric polycarboxylic acid by filtration or centrifugation.

6. Recovering said polyol and said solvent by distillation.

7. Recombining said polyol and said polycarboxylic acid to reform the said polyalkylene phthalate polyester resin by polyesterification. Fresh polyol may be added, if necessary, to obtain stoichiometry in the polyesterification reaction.

In the above process, whenever water is used as the slurrying medium or solvent, then a polycarboxylic acid is produced, for example, terephthalic acid (TA). Whenever the slurrying medium is a lower alkanol, such as methanol, then a dialkyl phthalate is formed, for example, dimethyl terephthalate (DMT). Alkanols of a higher molecular weight than methanol are preferably not utilized as a solvent in the instant process. Diols and polyols are not utilized as a solvent in the recovery process of the instant invention inasmuch as their use would result in extraneous esterification reactions in the latter steps of the process or in difficult separation steps.

In the above process, the recovery of the polycarboxylic acid and polyol, for example, ethylene glycol, the recycling of the solvent and the conservation of energy in the process are important aspects.

Further understanding of the invention may be facilitated by reference to FIG. 1.

In FIG. 1, a stream 10 of solid chunks of waste polyethylene terephthalate (PET) are fed to a granulator 11. The material exiting the granulator is conveyed 12 to a hopper 13 for storage. The particles departing the granulator have a mean particle size of about one-eighth inch in thickness. The particles are conveyed from hopper 13 via a belt conveyer, screw conveyor or the like into a slurry drum 14 wherein the particles of PET are slurried with water or methanol to a concentration of about 10% to about 40% and preferably from about 20% to about 30% by weight solids. From the slurry drum 14, the material is pumped serially through heat exchangers 15 and 16 to raise the temperature of the slurry of PET to a temperature in excess of about 350° F., but generally not exceeding about 550° F. Heat exchanger 15 is preferably a solvent vapor heat exchanger, while heat exchanger 16 is preferably a hot oil heat exchanger but may be a high pressure steam heat exchanger.

The material flowing through the heat exchanger has a solids concentration of about 20% to about 30% PET. The hot slurried PET is fed into a depolymerizer 17, which is operated at a temperature of about 350° F. to about 550° F. at an internal pressure of about 350 psig to about 1,500 psig. A liquid state reaction, namely, hydrolysis or methanolysis, occurs between the solvent, e.g. water or methanol, and the PET in the depolymerizer. Typical residence time of the reaction mixture in the depolymerizer is about 15 minutes to about one hour. Substantially complete hydrolysis or methanolysis of the PET occurs in the depolymerizer.

Exiting the depolymerizer 17 is a liquid stream 18 of terephthalic acid or dimethyl terephthalate, ethylene glycol, and solvent. Some small amount of granulated scrap PET may be present; however, this amount should be very minimal providing the proper temperatures, pressures, and residence times are maintained in the depolymerizer. In the event any significant amount of solids are present in stream 18, then stream 18 is generally directed through carbon bed 19 to remove any solids and to absorb any impurities.

Liquid stream 20 flows from carbon bed 19 and is fed to a flash crystallizer 21 which is operated at or near atmospheric pressure. In the depolymerization process, typically hydrolysis or methanolysis, for each approximately 200 pounds of polyethylene terephthalate (PET) present there is required about 37 to 38 pounds of water to participate in the hydrolysis reaction, which involves hydrolizing of the polyester into its monomeric components. For the same amount of PET, if methanol is the solvent, then about 66 to 67 pounds of methanol would participate in the methanolysis reaction to form a polyol and a low molecular weight diester monomer such as dimethyl terephthalate (DMT). Thus, only a portion of the solvent present participates in the depolymerization reaction. No reactant other than the solvent, however, is required to be present. Stream 20 proceeding to the crystallizer therefore contains a large volume of excess solvent.

In the flash crystallizer, the solvent vapor which flashes off is recovered in heat exchanger 15. The flash crystallizer is operated at a temperature of about 460° F. down to about 150° F. so that the stream 22 exiting the flash crystallizer has a temperature of about 150° F. to 200° F. Stream 22 is substantially a slurry of crystals of terephthalic acid or DMT in a solution of solvent and ethylene glycol. For purposes of simplicity, the remaining description of the process will assume that water is the solvent.

Although the description of crystallizer 21 refers to it in the singular, it is to be understood that one or more crystallizer vessels may be utilized in series or parallel. Unless otherwise specified, all such indications of a particular type of equipment used in the described process should be understood to mean at least one such piece of equipment. The selection of one or more pieces of equipment will depend upon volume throughput of the plant and the desirability of staging a certain process step. In the specific instance of the crystallization step, one or more crystallizer vessels in series may be desirable since a descending operating temperature is desired.

Terephthalic acid crystals produced in the crystallizer are transported as a slurry in a solution or miscible mixture of ethylene glycol (EG) and water, comprising stream 22 which is fed to a solids separator 23, which may be a conventional filter, centrifuge, or other filtration apparatus for effectively filtering out the solid terephthalic acid particles. Some recovered ethylene glycol is used to wash the solid terephthalic acid particles in solids washer 23A. The solid particles of terephthalic acid are fed to a polycondensation reactor 25. The filtrate of ethylene glycol and water, combined with the ethylene glycol wash liquor from the solids washer 23A, is fed to a distillation feed drum 27.

The solids washer 23A receives recovered ethylene glycol through conduit 28 as wash liquor for washing the water and ethylene glycol solution entrained on the terephthalic acid crystals to eliminate substantially the presence of water on the crystals. Any water originally entrained with the terephthalic acid crystals will be collected in distillation feed drum 27 along with ethylene glycol. From distillation feed drum 27, conduit 29 carries the filtrate and wash liquor, combined with condensed ethylene glycol vapor and condensed water vapor from polycondensation reactor 25, over to the solvent recovery tower 30.

Since only a portion of the water present in the flash crystallizer actually flashes, that is, evaporates in the crystallizer, a significant amount of the water passes from the bottom of the crystallizer through line 22, through the solids separator 23, and into the distillation feed drum. Thus, in the distillation feed drum 27, there is an admixture of water and ethylene glycol. The water and ethylene glycol mixture is transported from the distillation feed drum through conduit 29 to the water recovery tower 30. Water recovery tower 30 is a distillation tower operated at a temperature of about 330° F. and a pressure of about 90 psig. Water distills from the tower at the top and passes through line 31 to a water condensor 32. Water from the water condensor is returned to a water reflux drum 33. Water from the water reflux drum is split, with a portion returning to line 34 to pass down through the distillation column of the water recovery tower 30 as reflux. Through line 35, a portion of the water is passed through a heat exchanger 36 whereby it is cooled to return through line 37 to the water slurry drum 14. Fresh water make-up 38 is added to conduit 37 to maintain a constant ratio of water to PET entering the slurry drum 14.

Glycol removed from the bottom of water recovery tower 30 flows to ethylene glycol recovery tower 39, which is a distillation column operated at a temperature of about 400° F. and a pressure of about 50 psig. The purpose of this tower is to recover pure ethylene glycol from the top of the tower and have any residual catalyst, pigments and/or other materials which may have been originally within the original, solid, scrap PET, along with any higher boiling polyols, exit from the bottom of the tower. Thus, through line 40 exits essentially pure ethylene glycol vapor which passes through an ethylene glycol condensor 41 wherein it is condensed and then transported as a liquid through line 42 to ethylene glycol reflux drum 43. A portion of the ethylene glycol is recycled through line 44 to the ethylene glycol recovery tower 39 with the remainder of the ethylene glycol being transported through line 38 to the solids washer 23A. Fresh ethylene glycol make-up 45 is added to stream 28 to maintain a constant flow of ethylene glycol wash to solids washer 23A.

The bottom stream exits tower 39 through line 46 and through a thin film evaporator 47 which returns any ethylene glycol present through stream 48 to the tower. A portion of the bottom stream is recycled through line 49 through boiler 50 and returned to the tower to maintain the desired temperature range within the tower. Through line 51 is transported the residue which comprises catalysts, dies, pigments, fillers, higher boiling polyols, etc. which may have been in the original PET waste. This material may be generally incinerated.

In the ethylene glycol-wet solids stream 24 leaving the solids separator 23, approximately stoichiometric quantities of terephthalic acid and ethylene glycol are present for the purpose of being polyesterified to produce polyethylene terephthalate. The ethylene glycol-wet solids mixture is fed to a polyesterification reactor 25, which operates at a temperature of about 350° F. to about 500° F. and at a pressure of about atmospheric up to about 10 psi gage pressure and down to a subatmospheric pressure of about 50 microns. If needed, additional recovered ethylene glycol is fed to polycondensation reactor 25 through conduit 28A to balance the ethylene glycol requirements of polycondensation. The polyesterification reaction occurs to produce polyethylene terephthalate, which exits from the reactor through line 52 to proceed to a pelletizer 53 wherein the polethylene terephthalate is cooled, chipped and sent to storage through line 54. Because of the temperature and pressure of operation in the polyesterification reactor 25 and the polycondensation reaction occurring therein, the water of condensation and some ethylene glycol will vaporize and be transported by line 55 to the distillation feed drum 27.

The water conveyed through line 55 exiting the polyesterification reactor is the water of condensation which occurs in the esterification reaction between the terephthalic acid and the ethylene glycol. One molecule of water will be produced for each acid group-hydroxyl group reaction (condensation reaction) which occurs in the polyesterification reactor.

If the polyethylene terephthalate material produced in the polyesterification reactor has an average molecular weight which is approximately the same as the waste PET which is fed to granulator 11, and further assuming that in the depolymerizer 17 there is substantially complete hydrolysis; then if the approximate weight per unit time (throughput) of polyethylene terephthalate which is hydrolized in the depolymerizer is substantially equivalent to the same weight of polyethylene terephthalate produced in the polyesterification reactor, the water of condensation produced in the polyesterification reactor is substantially the same as the amount of water which is consumed in the depolymerizer in hydrolyzing the PET to produce the monomers terephthalic acid and ethylene glycol.

The polyesterification reactor may actually be a series of vessels if the polyesterification procedure is a continuous procedure.

The PET produced in the polycondensation reactor preferably has an intrinsic viscosity of about 0.5 to about 1.0. Reaction conditions and residence time are controlled to provide the preferred intrinsic viscosity.

The pressure and temperature conditions for the PET polycondensation reactor are those required for forming PET from terephthalic acid and glycol. In the event the depolymerization process uses methanol as a solvent in lieu of water so that dimethyl terephthalate is utilized as a monomer in the polycondensation reactor, then a transesterification reaction, rather than a condensation reaction, will occur whereby methanol will be a by-product of the reaction and will exit through line 55. However, the temperature and pressure conditions will be essentially the same but their sequencing over the reaction time may be different.

For the case when methanol is the solvent, the temperature in the solvent recovery tower 30 will be somewhat lower than the case when the solvent is water.

The invention described herein is particularly advantageous as a technique for recovering the chemical value of scrap PET. Complete depolymerization of solid, scrap PET to its basic building blocks, namely, ethylene glycol and terephthalic acid or dimethyl terephthalate, while conserving energy and recycling of all essential materials provides complete flexibility as to the type of end product the reconstituted PET can be used to form. Furthermore, the monomers are essentially pure and can be readily admixed with fresh monomers for production of PET.

Complete depolymerization produces monomers which are soluble in the respective solvents, i.e. water and methanol, at the temperatures involved in the depolymerization reaction. Solid materials in the PET, e.g. catalysts, stabilizers, pigments, etc. are substantially completely removed in the instant process. Thus, the monomeric components formed by the instant process have substantially the same purity as fresh monomers and may be utilized in the same manner as fresh monomers. Also, the instant process is substantially self-sustaining inasmuch as virgin PET resin may be produced of substantially any intrinsic viscosity without addition of any substantial addition of fresh monomer. Typically, some slight diminishment of ethylene glycol may occur by discharge from the thin film evaporator with residue, however, if desired, an equivalent amount of terephthalic acid could be directed to the incinerator for disposal along with pigments, catalysts, etc. so that no fresh monomer of any kind is required in order to have equimolar quantities of the reactants entering the polycondensation reactor.

The present process is essentially a liquid-state process. The solid waste PET is granulated to a size whereby it can be readily pumped as a slurry in water or methanol. Also, tne crystallized terephthalic acid or DMT departing the crystallizer is handled as a slurry. Only the wet solids exiting the solids separator may require propulsion means other than a pump; e.g., a slurry screw conveyor or the like.

A significant advantage of the instant process resides in the use of water or methanol as a solvent and as a liquid medium for the slurried solids. Water is especially useful since it is readily available in pure form, is especially miscible with ethylene glycol and is a good solvent at elevated temperatures for terephthalic acid. Both water and methanol are readily separable from ethylene glycol by distillation.

Very minor concentrations of ethylene glycol in the solvent, or vice versa, are not detrimental to the operation of the process. Also, recycling of the solvent tends to retain within the system any ethylene glycol coming over with the solvent in the solvent recovery tower.

I claim:

1. A process for recovering monomeric phthalic polycarboxylic acids or dimethyl ester thereof and low molecular weight polyols from solid scrap high molecular weight polyalkylene phthalate polyester resins comprising:
    granulating said scrap resin into resin particles sufficiently minute to be readily slurried;
    slurrying said granulated scrap resin particles with sufficient solvent to prepare a readily pumpable slurry, said solvent selected from the class consisting of water and methanol in which a low molecular weight polyol is soluble;
    depolymerizing said slurried resin at a temperature, pressure and for a time sufficient to convert substantially all of said resin into its monomeric components in liquid form in a hydrolized or methanolized mixture; and
    crystallizing substantially all of the monomeric polycarboxylic acid monomer present in said hydrolized or methanolized mixture by flash crystallizing said mixture.

2. The process of claim 1 wherein said solvent is water.

3. The process of claim 1 wherein said solvent is methanol.

4. The process of claim 1 wherein the crystallized monomeric polycarboxylic acid is physically separated from said liquid polyol and liquid solvent.

5. The process of claim 4 wherein the separated polyol is first distilled to remove said solvent and distilled a second time to remove impurities.

6. The process of claim 5 wherein said distilled polyol with additional make-up polyol is fed, along with said monomeric phthalic acid from said physical separation step, in substantially stoichiometric proportions, to a polycondensation reactor to form a said high molecular weight polyalkylene phthalate polyester resin.

7. The process of claim 6 wherein solvent produced by the condensation reaction occurring in said polycondensation reactor is combined with said liquid polyol and liquid solvent exiting said solids separator.

8. The process of claim 5 wherein solvent distilled from said polyol is returned, with fresh make-up solvent as needed to slurry said granulated scrap resin particles.

9. The process of claim 8 wherein said slurry of granulated scrap resin particles has a solids content of from about 10% to about 40% by weight.

10. The process of claim 1 wherein said temperature is at least 350° F.

11. The process of claim 10 where said pressure is at least 350 psig.

12. The process of claim 1 wherein said polyalkylene phthalate polyester is a linear polyester.

13. The process of claim 12 wherein said linear polyester is polyethylene terephthalate.

14. The process of claim 12 wherein said polyol is ethylene glycol.

15. The process of claim 12 wherein said monomeric phthalic polycarboxlic acid is terephthalic acid.

16. The process of claim 12 wherein said monomeric phthalic polycarboxlic acid dimethyl ester is dimethyl terephthalate.

17. The process of claim 11 wherein said temperature is less than about 550° F.

18. The process of claim 11 wherein said pressure is less than about 1500 psig.

19. A process for recovering monomeric terephthalic acid or dimethyl terephthalate and ethylene glycol from solid scrap high molecular weight polyethylene terephthalate resin comprising:
    slurrying very finely granulated resin particles with sufficient solvent to prepare a readily pumpable slurry, said solvent being water or methanol;
    depolymerizing said slurried resin by heating to a temperature of at least about 350° F. and pressurizing to a pressure of at least about 350 psig. for a period of time sufficient to convert substantially all of said resin into its monomeric components in liquid form as ethylene glycol and terephthalic acid or dimethyl terephthalate in a liquid mixture; and
    crystallizing all of said terephthalic acid or dimethyl terephthalate present in said liquid mixture by flash crystallizing said mixture.

20. The process of claim 19 wherein said flash crystallization is conducted at a temperature of at least about 150° F.

21. The process of claim 19 wherein said crystallized terephthalic acid or dimethyl terephthalate is separated from said ethylene glycol by filtration means.

22. The process of claim 21 wherein the ethylene glycol is first distilled to remove said solvent, distilled a second time to remove impurities, then combined with make-up ethylene glycol and monomeric terephthalic acid or dimethyl terephthalate from said separation step, in substantially stoichiometric proportions, in a polycondensation reactor to form a high molecular weight polyethylene terephthalate resin.

* * * * *